(12) United States Patent
Reber

(10) Patent No.: US 7,634,094 B2  
(45) Date of Patent: Dec. 15, 2009

(54) METHOD FOR OBTAINING REAL EAR MEASUREMENTS USING A HEARING AID

(75) Inventor: Monika Bertges Reber, Berne (CH)

(73) Assignee: Bernafon AG, Berne (CH)

(*) Notice: Subject to any disclaimer, the term of this patent is extended or adjusted under 35 U.S.C. 154(b) by 864 days.

(21) Appl. No.: 11/208,010

(22) Filed: Aug. 22, 2005

(65) Prior Publication Data

US 2006/0045282 A1    Mar. 2, 2006

(30) Foreign Application Priority Data

Aug. 24, 2004    (EP) .................................. 04388057

(51) Int. Cl.
*H04R 25/00* (2006.01)
(52) U.S. Cl. ........................ 381/60; 281/312
(58) Field of Classification Search ................ 381/56, 381/60, 322, 328, 330, 338, 382, 312; 73/585; 600/559; 181/129, 130, 135
See application file for complete search history.

(56) References Cited

U.S. PATENT DOCUMENTS 4,827,525 A * 5/1989 Hotvet et al. ................ 381/60
5,386,475 A * 1/1995 Birck et al. ................ 381/320
6,118,877 A   9/2000 Lindemann
6,154,546 A   11/2000 Uvacek
2002/0176584 A1   11/2002 Kates

FOREIGN PATENT DOCUMENTS

CH         678692         10/1991

* cited by examiner

*Primary Examiner*—Huyen D Le
(74) *Attorney, Agent, or Firm*—Dykema Gossett PLLC

(57) ABSTRACT

The invention regards a method for measuring audio response of a real ear using the microphone of a hearing aid of an end user. The following sequence of steps is performed: provide a sound tight connection between the hearing aid microphone and a first end of a soundguiding flexible tube, disable any further microphones in the hearing aid, place a second end of the tube at the location wherefrom sound is to be captured, provide an audio sound signal at the area of the second end of the tube and record the sound guided through the tube to the microphone of the hearing aid, process the recorded sounds to retrieve sound level values. Hereby real ear measurements may be gained with a hearing aid with only one microphone without any additional measuring equipment.

2 Claims, 4 Drawing Sheets

METHOD FOR OBTAINING REAL EAR MEASUREMENTS USING A HEARING AID

AREA OF THE INVENTION

The invention concerns the obtaining of data relating to the impact a hearing aid has on the sound pressure in front of the tympanic membrane when the hearing aid is producing sound.

BACKGROUND OF THE INVENTION

In prior art document U.S. Pat. No. 6,154,546 it is known to apply a tube connected to one of the microphones in a directional digital hearing aid with more than one microphone. According to the patent the probe tube is adapted to be fitted inside the ear of the patient and to convey sound signals there from to one of the microphones of the hearing aid. When this system is used, two microphones are necessary as one microphone is to sense the conditions in front of the tympanic membrane while the other microphone at the same time will record the sound level at the ear.

From U.S. Pat. No. 6,118,877 it is further known to make use of a tone generator in the hearing aid to produce audio sounds for testing purposes.

With the prior art hearing aids and methods it is not possible to make real ear measurements with only one microphone.

Other known ways of making real ear measurements involve the use of further microphone modules and tubes and further electric leads connecting the microphone modules with the fitting unit. This is not much liked by hearing aid dispensers. Thus many hearing aids are dispensed without real ear measurements, and the values used in the fitting procedure are not verified. The invention seeks to solve this problem by providing a real ear measurement solution which does not require more electric wires or other components which the dispenser needs to operate. Further it is the object of the invention to provide a measurement method which can be performed with hearing aids with only one microphone and wherein the measurement is performed with the hearing aid instrument itself, such that more precise and reliable data are gained.

SUMMARY OF THE INVENTION

The invention regards a method for measuring audio response of a real ear using the microphone of a hearing aid of an end user. According to the method the following sequence of steps are performed: provide a sound tight connection between the hearing aid microphone and a first end of a soundguiding flexible tube, disable any further microphones in the hearing aid, place a second end of the tube at the location wherefrom sound is to be captured, provide an audio sound signal at the area of the second end of the tube and record the sound guided through the tube to the microphone of the hearing aid, process the recorded sounds to retrieve sound level values. The above sequence of steps is performed either one time while placing the second end of the tube near the tympanic membrane of the hearing aid user or performed two times with the second end of the tube at a reference point and near the tympanic membrane of the hearing aid user respectively.

By using the hearing aid microphone for the measurements and use the level meter which is already present in modem digital hearing aids it becomes possible to obtain data relating to the real ear wherein the hearing aid is going to function, and thus an easy way of improving the adaptation of the hearing aid to the individual is provided. The fact that the method can be used without further leads or connections and without expensive accessories will make this method more widely used, and in the end it will improve the comfort and benefit experienced by the end user of the hearing aid.

In an embodiment of the invention, the second end of the tube is placed near the microphone inlet of the hearing aid this being the reference point during the first time the sequence of steps is performed and further the second end of the tube is placed near the tympanic membrane during the second time the sequence of steps is performed. According to this embodiment, the ear canal is otherwise left open, and the sound signal at both the first and the second time the sequence of steps is performed is provided from a source outside the hearing aid. In this way an easy and straight forward way of obtaining REUG data is provided, where the dispenser uses a minimum of extra equipment namely the tube connecting the one microphone with the reference point and the area in front of the tympanic membrane respectively and a loudspeaker. The connection between the hearing aid and the fitting device is established anyhow and a program with the necessary alterations to handle the measurement and the loudspeaker is easily established. The difference between the two measurement results are not influenced by tube and external signal as long as the tube and the test signal are the same for both measurements. Thus more precise and accurate data on the REUG may be obtained when using the method according to the invention.

In a further embodiment the second end of the tube is connected to the inside volume of a coupler in a test box, this being the reference point, during the first time the sequence of steps is performed and the second end of the tube is placed near the tympanic membrane with the hearing aid or ear mould in place in the ear canal with possible venting canal blocked during the second time the sequence of steps is performed. The sound used for both the first and the second time the sequence of steps is performed is provided by the hearing aid receiver. According to this embodiment the invention allows RECD data to be obtained. In the cause of the first measurement in the coupler, the hearing aid is not connected to the fitting device, and the measurement data are stored inside a memory space in the hearing aid. The data is used after the second measurement, when the hearing aid is placed at the ear of the final user, and the same measurement is performed at the real ear. The difference between the two data sets allows a fine tuning of the hearing aid, which accounts for the difference between the response of the coupler and the response of the real ear of the user. All of this can essentially be gained with the simple tube connection between the hearing aid microphone and the surrounding along with simple fitting tool alterations to account for the extra measurement.

In a further embodiment the sequence of steps is performed once with the second end of the tube near the tympanic membrane, and with the hearing aid or ear mould in the ear. In this measurement the sound is generated by the hearing aid. This measurement can give an idea of the REAR, provided the microphone to receiver transfer function of the hearing aid is known. This transfer function or a good approximation thereof is usually easy to establish and thus the simple measurement can give a good estimate of the REAR response without having to provide extra measuring units and well controlled sound environments.

With these new measurement procedures it will be possible to incorporate the measurements in the fitting software to get a match to Insertion gain. Also the REUG values can be used more efficient in a fitting algorithm as it can be obtained with exact same hearing aid which the end user is going to receive. A further advantage of the proposed method is that the test signal used for the RECD measurement may be used to perform a usability test of the instrument in the ear during wearing. The function is simply to be called up by the end-user to ensure proper functionality.

DESCRIPTION OF A PREFERRED EMBODIMENT

In a first aspect of the invention Real Ear Unaided Gain or REUG data is obtained using the hearing aid as the measuring instrument. To measure REUG, a sequential measurement in free field of an identical noise signal is required. As explained, prior art measurements are performed with dedicated microphones which at the same time samples sound from inside the ear, usually by use of a small tube placed inside the ear, and from a reference point outside the ear.

Figure 1:
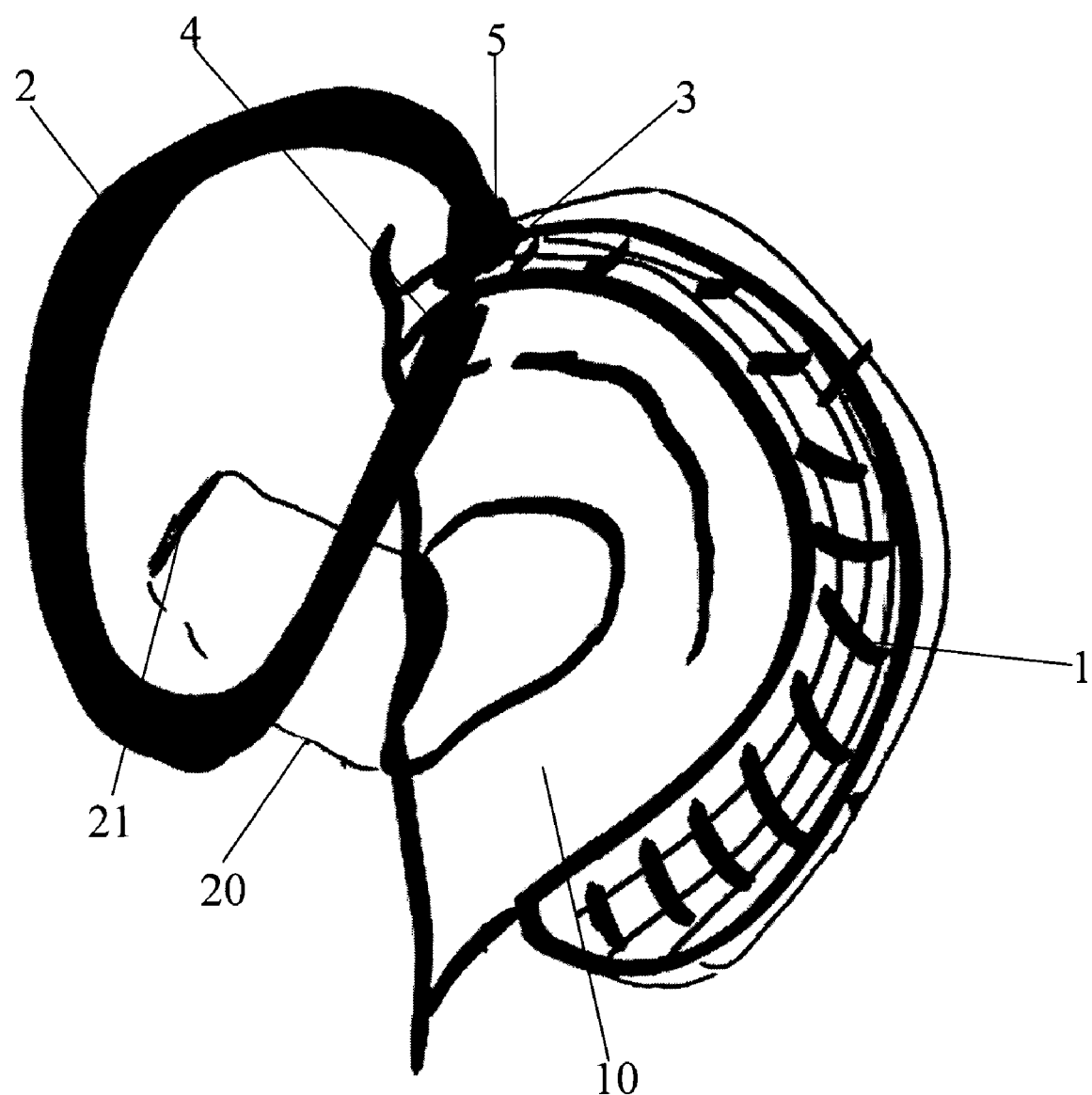
FIG. 1 displays REUG, measurement 1 from the area near the microphone.
Figure 2:
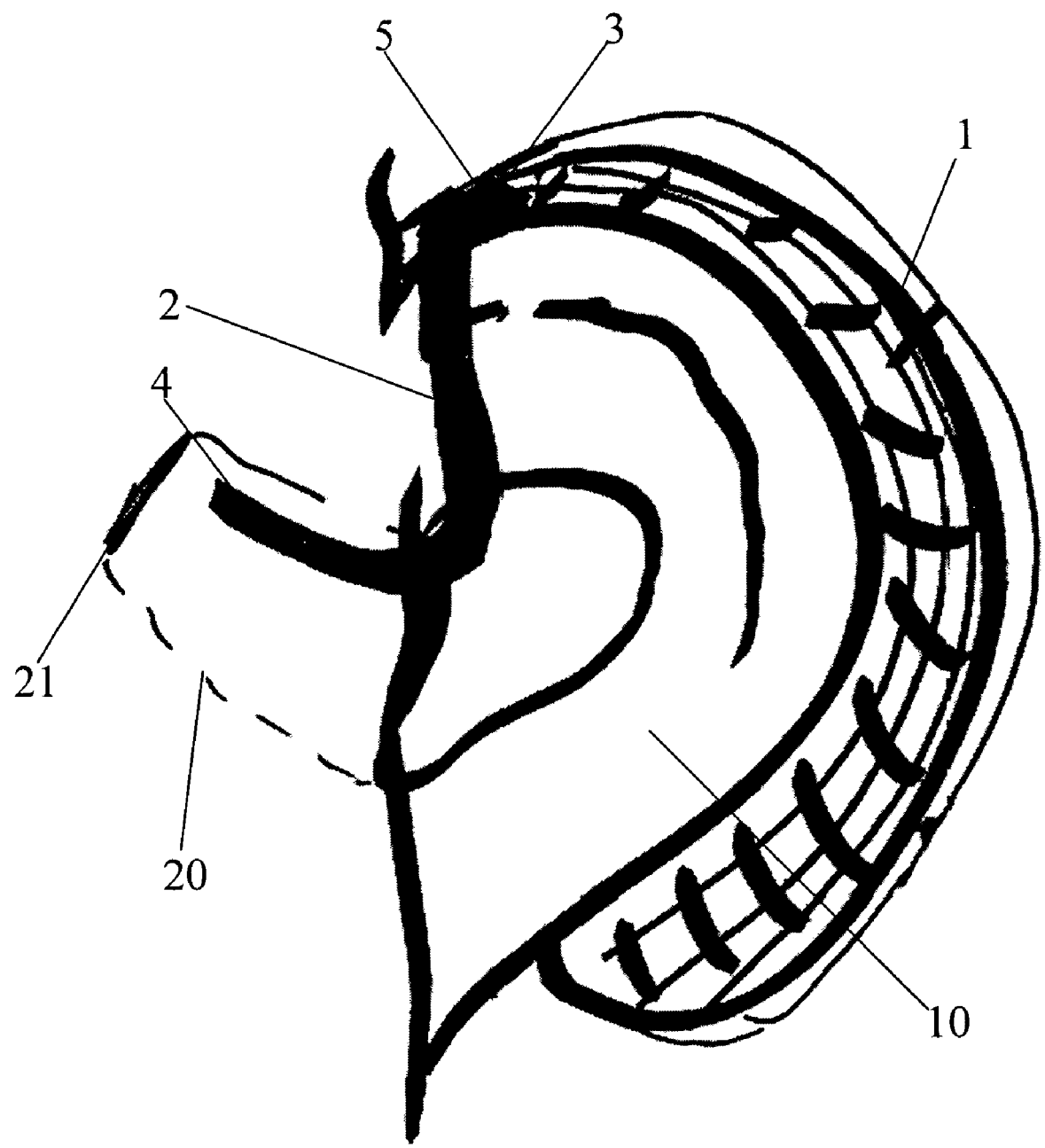
FIG. 2 is REUG, measurement 2 from the area near the tympanic membrane.

As shown in FIGS. 1 and 2 a sequential measurement is used according to the invention. The reference measurement outside the ear is illustrated in FIG. 1. Here a BTE (behind the ear hearing aid) 1 is placed at the ear 10. A tube 2 is connected at a first end 5 to the microphone inlet 3 of the BTE 1 and the other end 4 of the tube 2 is placed at the reference position. This reference position is right at the microphone inlet 3 of the BTE 1. The hearing aid 1 will be connected to a PC or other fitting device (not shown) in order to control the measurement and capture the measurement data. This connection can be a wired connection or a wireless link. During the measurement a controlled noise signal is supplied, preferably by a loudspeaker (not shown) and controlled by the fitting device. The noise signal is preferably a narrowband noise in each mid frequency which is sequentially supplied in each frequency band or channel of the hearing aid 1. The signal levels based on the signal level meter value from the signal level meter in the hearing aid 1 are measured in each available channel.

In FIG. 2 it is illustrated how the second part of the measurement takes place. Here the second end 4 of the tube 2 is placed inside the ear canal 20, which is otherwise open, and the same noise signal is supplied and the same measurement is performed using the level meter of the hearing aid 1. The tube end 4 is placed near the tympanic membrane 21, as usually prescribed. This can be converted to REUG data simply by subtracting the first measured loudness from the second measured loudness in each channel. All which is required to perform this is the tube 2 and the connection possibility between the hearing aid microphone inlet 3 and the tube 2 and a signal level meter in the hearing aid 1, along with the loudspeaker. Further the fitting device must have a suitable program for generating the noise signals and for controlling the measurement. The measured levels can be either routed to the fitting device during the measurement procedure or stored in a register in the hearing aid 1 for later access by the fitting device.

Figure 3:
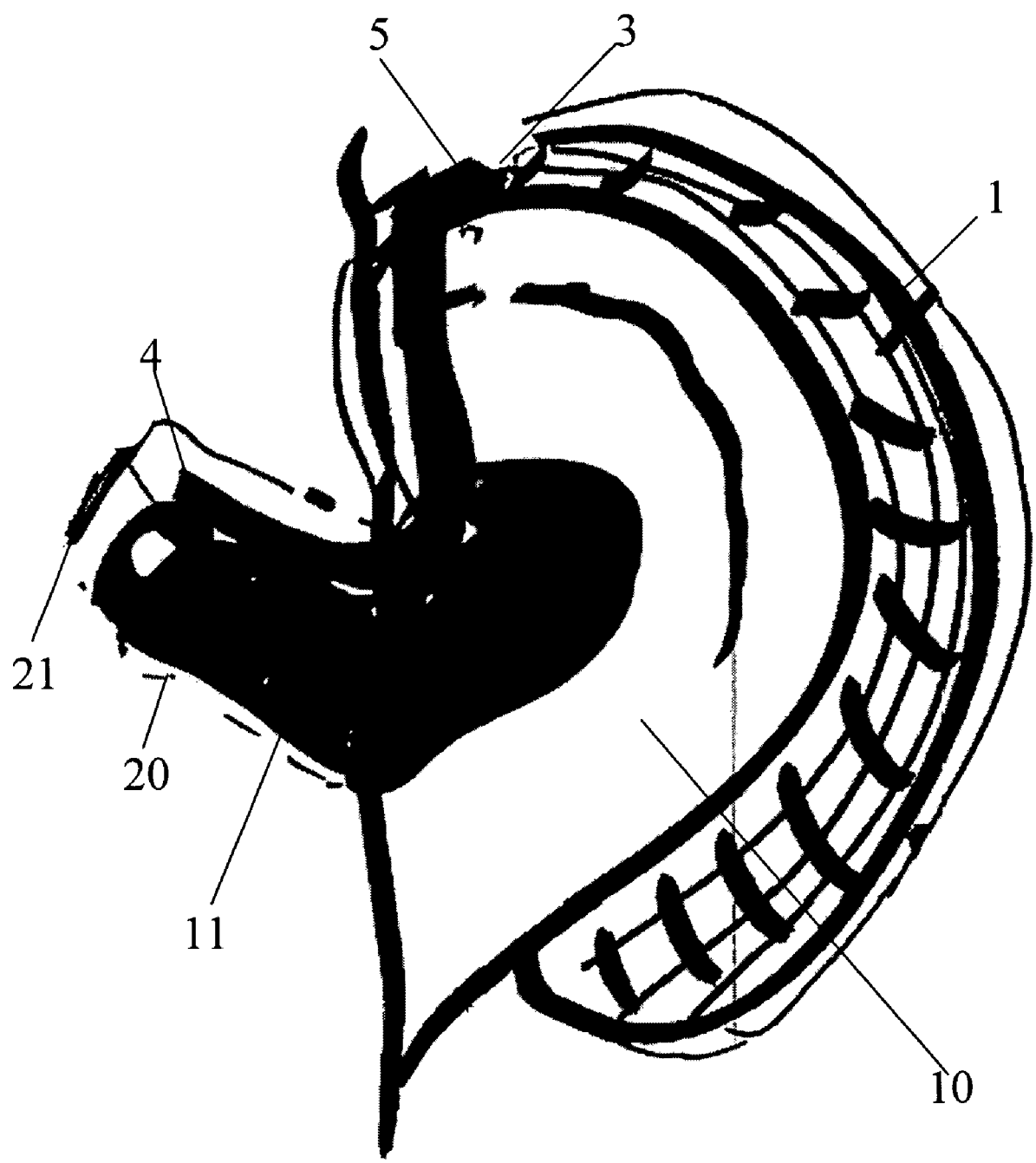
FIG. 3 is REAR where the hearing aid or ear mould in the ear, also used when gaining RECD measurements.

In a further embodiment of the invention REAR measurement data are obtained using the hearing aid 1. This is illustrated in FIG. 3. REAR meaning Real Ear Aided Response is usually a straight measurement, where 2 microphones at the same time are used, and such that the first microphone measures the sound levels outside the ear at the point where the microphone of the hearing aid is placed and the other measures the sound level caused by the hearing aid inside the ear in front of the tympanic membrane. The two signals are then subtracted from one another to give the REAR data. But according to the invention the REAR is obtained with the use of only one microphone. This is achieved by sending audio signals to the hearing 1 aid from the fitting device and then provide the signal to the receiver which will play the sound inside the ear canal 20. As seen in FIG. 3 the ear mould 11 or ITE hearing aid is in place in the ear canal 20 during measurements. At the same time the microphone via the tube connection 2 is used to measure the sound level inside the ear canal 20 in front of the tympanic membrane 21. During the measurement the signal captured by the microphone is stored and processed to give the REAR data.

Before the REAR data can be retrieved it is necessary to know what the sound level outside the hearing aid would have been in order to produce the sound played by the receiver. This is done by verifying the microphone to audio signal transfer function and then a correction can account for the difference when using direct audio input or via the programming interface to the hearing aid instead of a microphone input. The correction may be based on a default value for a specific microphone type usually supplied by the microphone manufacturer. Further, the vent needs to be open just as in a regular wearing condition.

In this way it becomes possible to do REAR measurements on instruments with only one microphone.

Figure 4:
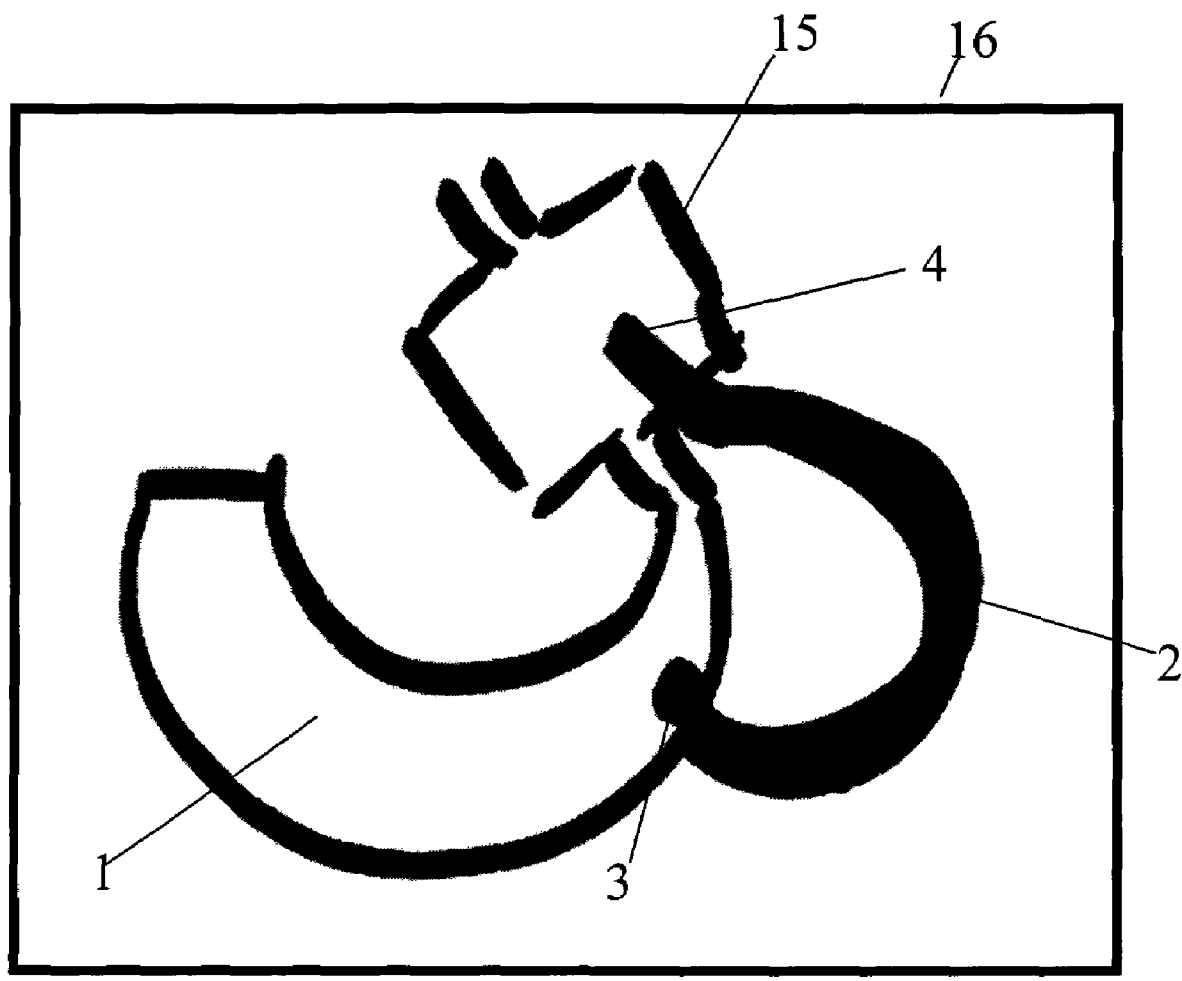
FIG. 4 is RECD, measurement 1 with the tube in the coupler.

In a further embodiment of the invention Real Ear to Coupler Difference data (RECD) are obtained using the hearing aid. This is illustrated in FIGS. 3 and 4.

In order to obtain a RECD according to the invention measurements at two different points in time are required whereby the signal generator of the hearing aid 1 plays the same signal. One measurement has to be performed with the tube 2 in a coupler 15 and a second measurement with the tube end 4 within 5 mm in front of the tympanic membrane 21 of the end user where the hearing aid receiver at both measurements is caused to play a sound. In the first measurement the hearing aid 1 and coupler 15 is placed in a sound-tight measuring box 16 as shown in FIG. 4. Such a box and the coupler is standard equipment at most production facilities. During the second measurement the ear canal 20 is blocked by the ear mould 6 or an ITE hearing aid and also a possible vent-hole is blocked. The difference between the two measurement results gives the RECD. The second measurement is essentially the same as goes on when capturing REAR data and is illustrated in FIG. 3. The coupler is a standard element which simulates the acoustic properties of the volume inside an average ear.

The invention claimed is:

1. A method of measuring audio response of a real ear using a microphone of a hearing aid of an end user, comprising the following steps in a first sequence:
   (a) providing a sound tight connection between the microphone and a first end of a flexible sound guiding tube,
   (b) disabling any further microphones in the hearing aid,
   (c) placing a second end of the sound guiding tube at a location wherefrom sound is to be captured,
   (d) providing an audio sound signal at the area of the second end of the tube and recording sound guided through the tube to the microphone of the hearing aid, (e) analyzing the recorded sounds to retrieve sound level values, wherein the first sequence of steps (a)-(d) are repeated in a second sequence, wherein during the first sequence of steps (a)-(d), the second end of the tube is placed near an inlet of the microphone, this being a reference point, wherein the second end of the tube is placed near a tympanic membrane during the second sequence of steps (a)-(d), and wherein the ear canal is otherwise left open, and wherein further the audio sound signal provided during both the first and second sequence of steps (a)-(d) from a source outside the hearing aid.

2. A method of measuring audio response of a real ear using a microphone of a hearing aid of an end user, comprising the following of steps in a first sequence:

(a) providing a sound tight connection between the microphone and a first end of a flexible sound guiding tube, (b) disabling any further microphones in the hearing aid, (c) placing a second end of the sound guiding tube at a location wherefrom sound is to be captured, (d) providing an audio sound signal at an area of the second end of the tube and recording sound guided through the tube to the microphone of the hearing aid, (e) analyzing the recorded sounds to retrieve sound level values, wherein the first sequence of steps (a)(d) are repeated in a second sequence, wherein during the first sequence of steps (a)-(d), the second end of the tube is connected to an inside volume of a coupler in a test box, this being a reference point, wherein during the second sequence of steps (a)(d), the second end of the tube is placed near a tympanic membrane with the hearing aid or ear mould in place in the ear canal with possible venting canal blocked, and wherein the audio sound signal provided during both the first and second sequence of steps (a)-(d), is provided by the hearing aid receiver.

\* \* \* \* \*